US008854623B2

(12) United States Patent
Fontaine et al.

(10) Patent No.: US 8,854,623 B2
(45) Date of Patent: Oct. 7, 2014

(54) SYSTEMS AND METHODS FOR MEASURING A PROFILE CHARACTERISTIC OF A GLASS SAMPLE

(71) Applicant: Corning Incorporated, Corning, NY (US)

(72) Inventors: Norman Henry Fontaine, Painted Post, NY (US); Vitor Marino Schneider, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/055,351

(22) Filed: Oct. 16, 2013

(65) Prior Publication Data

US 2014/0118740 A1    May 1, 2014

Related U.S. Application Data

(60) Provisional application No. 61/718,273, filed on Oct. 25, 2012.

(51) Int. Cl.
| | |
|---|---|
| *G01N 21/21* | (2006.01) |
| *G01N 21/41* | (2006.01) |
| *G01N 21/23* | (2006.01) |
| *G01L 1/24* | (2006.01) |
| *G01M 11/00* | (2006.01) |

(52) U.S. Cl.
CPC ............. *G01N 21/21* (2013.01); *G01N 21/412* (2013.01); *G01N 21/41* (2013.01); *G01N 21/23* (2013.01); *G01L 1/24* (2013.01); *G01M 11/30* (2013.01)
USPC ........................................................ 356/364

(58) Field of Classification Search
CPC ....... G01N 21/23; G01N 21/21; G01N 21/41; G01N 21/412; G01M 11/30; G01L 1/24
See application file for complete search history.

(56) References Cited

U.S. PATENT DOCUMENTS

| 5,280,334 A | 1/1994 | Gisin et al. ................... 356/73.1 |
| 7,317,517 B2 | 1/2008 | Junnarkar et al. ........... 356/73.1 |
| 2005/0024627 A1 | 2/2005 | Junnarkar et al. ........... 356/73.1 |
| 2005/0167578 A1* | 8/2005 | Riza et al. ..................... 250/234 |
| 2013/0221238 A1* | 8/2013 | Li et al. ....................... 250/459.1 |

OTHER PUBLICATIONS

Oh et al., Polarization-Sensitive Optical Coherence Tomography for photoeleasticity testing of glass/epoxy composites, 2003, Otpics Express, vol. 11, No. 14, pp. 1669-1676.*

(Continued)

*Primary Examiner* — Tarifur Chowdhury
*Assistant Examiner* — Juan D Valentin, II
(74) *Attorney, Agent, or Firm* — Robert P. Santandrea

(57) ABSTRACT

Systems and methods for measuring a profile of a glass sample (300) are disclosed. The method includes scanning a polarization-switched light beam (112PS) through the glass sample and a reference block (320) for different depths into the glass sample to define a transmitted polarization-switched light beam. The method also includes measuring an amount of power in the polarization-switched light beam to form a polarization-switched reference signal (SR), and detecting the transmitted polarization-switched light beam to form a polarization-switched detector signal (SD). The method further includes dividing the polarization-switched detector signal by the polarization-switched reference signal to define a normalized polarization-switched detector signal (SN). Processing the normalized polarization-switched detector signal determines the profile characteristic.

20 Claims, 10 Drawing Sheets

(56) References Cited

OTHER PUBLICATIONS

Norman H. Fontaine and Matt Young, "Two-dimensional index profiling of fibers and waveguides," Appl. Opt., vol. 38, No. 33, Nov. 20, 1999, pp. 6836-6844.

Irena Fryc, "Angular characteristics of a silicon detector spectral sensitivity corrected by an absorption filter," Proc. of SPIE vol. 4517 (2001), pp. 42-45.

R. Goring, M.Rothhardt, "Application of the Refracted Near-Field Technique to Multimode Planar and Channel Waveguides in Glass," J. Opt. Comm. 7 (1986) 82-85.

Gao et al.; "The Research of Measuring Special Optical Fiber Refractive Index Profiles by Refracted Near-Field Method"; Proceedings of SPIE, vol. 8202; Nov. 2011; pp. 82020Y-1-82020Y-7.

Loch et al.; "High-Resolution Measurement of Birefringence Profiles in Stress-Induced Polarization-Maintaining Fibers"; Journal of Lightwave Technology, vol. 7, No. 8; Aug. 1989; pp. 1213-1214.

Jestel et al.; "Refracted Near-Field Characterization of Ion Exchanged Glass Waveguides and Device Simulation"; Proceedings of the European Conference on Integrated Optics vol. 1141; Apr. 1989; pp. 185-190.

European Patent Office; International Search Report; Mailing Date: Jan. 22, 2014; pp. 1-4.

* cited by examiner

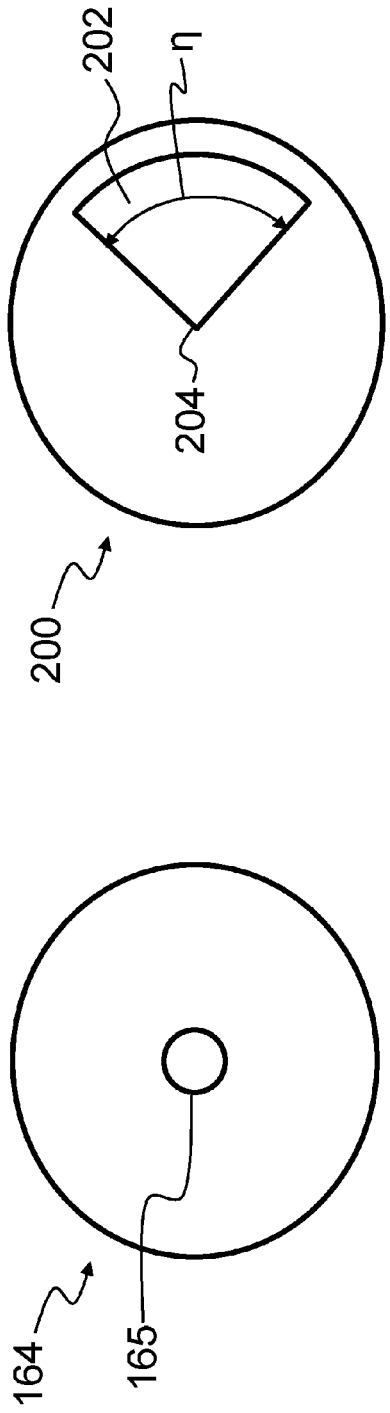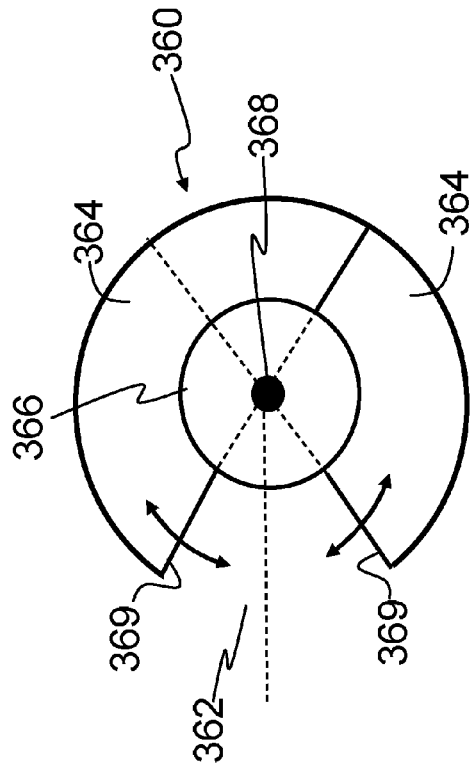

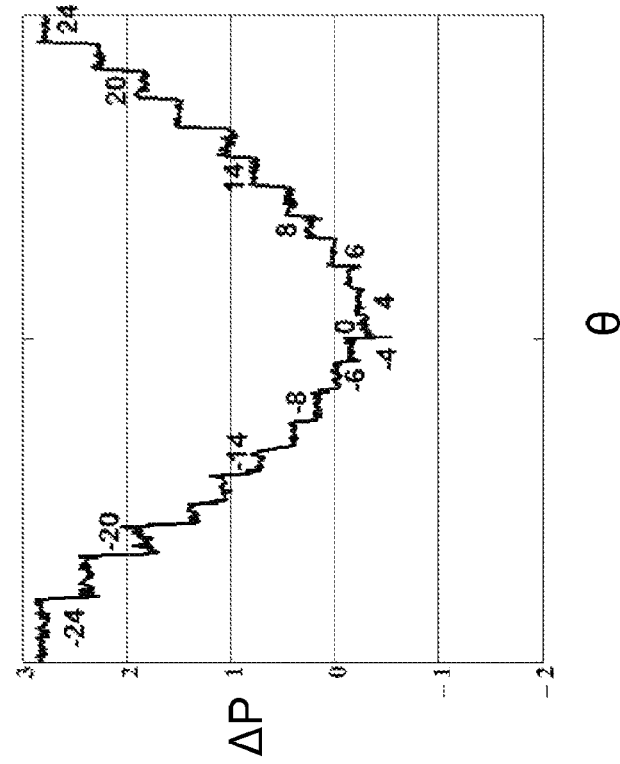
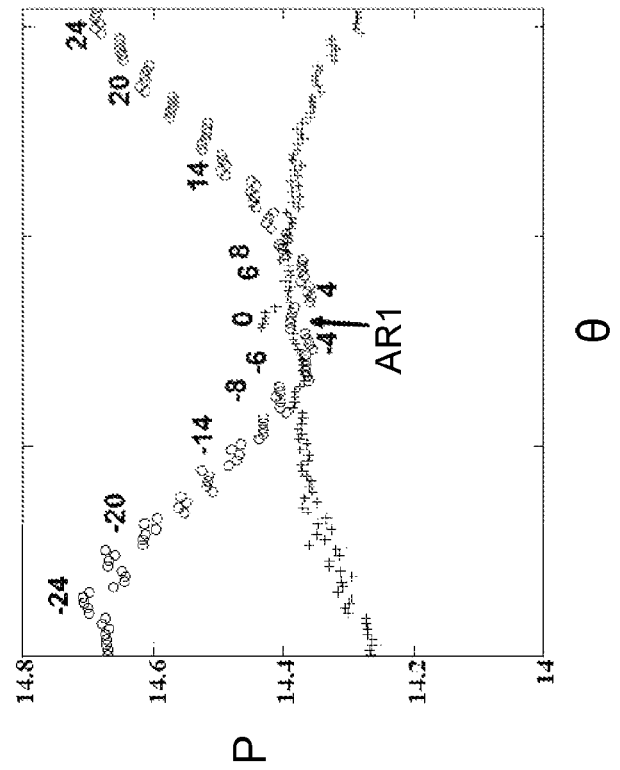
FIG. 5A
FIG. 5B

SYSTEMS AND METHODS FOR MEASURING A PROFILE CHARACTERISTIC OF A GLASS SAMPLE

This application claims the benefit of priority under 35 U.S.C. §119 of U.S. Provisional Application Ser. No. 61/718,273 filed on Oct. 25, 2012 the content of which is relied upon and incorporated herein by reference in its entirety.

FIELD

The present disclosure relates to systems and methods for optically characterizing glass, and in particular relates to systems and methods for measuring a profile characteristic of a glass sample.

BACKGROUND

Ion-exchange and other glass-strengthening processes can create stresses in the glass and give rise to optical birefringence. Compressive and tensile stress regions formed in the glass can have relatively small depths (e.g., 10 micrometers) or relatively large depths (e.g., a few or many millimeters). The stress profile of a glass part can be deduced from the measurement of the refractive index profiles for orthogonal polarizations of measurement light, with the difference in the index profiles for both polarization states representing the birefringence. The stress is related to the birefringence through the stress-optic coefficient. The character (profile) of the stress can be quite complex and depends on a number of factors, including the base glass material, the glass production processes and the down-stream manufacturing process.

The stresses in a glass part can be altered by various external forces, including how the glass part is mounted into a device and how the glass part is used. During reliability and failure-mode studies, various quality-control procedures are used to test and measure the change in stress across the edges and throughout the volume of the glass part.

One technique that has been used to measure refractive index and birefringence profiles (and thus stress) in ion-exchanged, planar optical waveguides is the refracted near-field (RNF) method. The RNF method utilizes a system wherein a reference block is in contact with the glass part being measured. Measurement light passes through the glass part and the reference block and is detected by a photodetector arranged very close to the top of the reference block. An example RNF system is disclosed in U.S. Pat. No. 5,280,334.

A problem with prior-art RNF systems is that the photodetector, besides detecting the measurement light, also detects scattered and multiply reflected light from many angles and locations. The scattered light may arise from imperfections in an index fluid (e.g., contaminants), on the surfaces of the reference block (e.g., dust leftover after sub-optimal cleaning), in the optics of the RNF system or even within the glass sample itself (e.g., bubbles and other "seeds"). Such scattered light may lead to erroneous measurements of the refracted power of the glass part.

SUMMARY

The disclosure is directed to RNF systems and methods for measuring a profile characteristic of a glass part (referred to herein a "glass sample"). Example profile characteristics are refractive index profiles for orthogonal polarizations of light, birefringence and stress. The systems and methods operate over an extended scan-depth range on the order of millimeters. The system has low thermal and temporal sensitivity to the birefringence measurement due to the nearly simultaneous measurement of the TE and TM states of polarization. This is achieved by using a polarization switch that rapidly (e.g., within one or a few milliseconds) switches the measurement light between TE and TM polarization at each measurement point as the measurement light scans the glass sample. This switching greatly reduces the sensitivity of the birefringence measurement to fluctuations in the optical power of the light source as well as to vibrations in the environment. It also eliminates the need for precise and scan-range-limiting positioning equipment, like piezoelectric scanners, which would otherwise be needed to precisely reposition both of the polarization scans in order to make an accurate stress measurement.

A power-monitoring reference photodetector is operated in synchrony with the signal photodetector to perform common-mode signal processing of polarization-switched reference and detector signals. This synchronous operation serves to normalize out fluctuations in the signal power from the light source as well as signal variations that arise from the polarization dependency of the power transmitted through the polarization switch. Confocal imaging methods are also used to reduce signal noise by blocking unwanted light (e.g., scattered and multiply reflected light) from reaching the signal and the reference detectors. This reduction in signal noise enables the refracted light signal that emanates from the point of the measurement of the glass sample to be interrogated in isolation.

The signal photodetector is positioned with its photosensing surface generally normal to and co-axial with the central ray of the beam incident thereon (roughly at the angles of $(\beta_{max}-\beta_{min})/2$, and $\eta=0$; FIG. 1). This positioning serves to eliminate most of the angular and polarization-dependent variations in detection efficiency that high-refractive-index semiconductor photodetectors exhibit when used at large incident angles. It also decreases the effective range of angles that are incident upon the signal photodetector by a factor of two. In addition, in this configuration the photodetector requires no specialized anti-reflection coatings to facilitate large-angle detection.

A second sectorial aperture stop allows the azimuthal range of angles to be stopped down to any desired angular range. This reduces or eliminates undesirable diffractive effects from the edges of a primary sectorial aperture stop. The second sectorial stop defines a minimum pass angle $\beta_{min}$ of a blocking disk. A maximum pass angle $\beta_{max}$ is not restricted by the second sectorial stop and depends upon the index of refraction at the focal point of the objective.

The second aperture stop is placed well above the top surface of the reference block, e.g., at a distance DS of 0.6 inches to 1.25 inches. The signal photodetector is located at an axial from the top of the reference block that is in the range from 80 mm to 200 mm. The distance from the sample to the first lens downstream therefrom is limited by the requirement that the clear aperture of the receive lens pair must be capable of accepting refracted light during a scan that may range from the minimum angle of $\beta_{min}$ and to the maximum angle of $\beta_{max}$ without vignetting any of the light that passes the second sectorial stop. For the example of a lens with a 2-inch diameter, this distance is approximately less than or equal to 80 mm.

An aspect of the disclosure is a system for performing a refracted near-field (RNF) measurement of a profile characteristic of a glass sample disposed adjacent a reference block having a top surface. The system includes a light-source system that generates polarized light, and a polarization-switching system that receives and switches the polarization of the polarized light between first and second orthogonal polarizations to form a polarization-switched light beam. The system also has a reference detector system arranged to receive a portion of the polarization-switched light beam and form a polarization-switched reference detector signal. An optical system is configured to scan the polarized-switched light beam through the glass sample and the reference block at different depths into the glass sample. A signal detector system is arranged to receive, over an angular range within 26° to 45° relative to normal incidence, the polarization-switched light beam transmitted through the glass sample and the reference block, and form in response a polarization-switched detector signal. A signal-control-and-processing system is operably configured to move the reference block and sample and receive and process the polarization-switched reference and detector signals to determine a profile characteristic of the glass sample.

Another aspect of the disclosure is a method of measuring a profile characteristic of a glass sample disposed adjacent a reference block having a top surface. The method includes scanning a polarization-switched light beam through the glass sample and the reference block for different depths into the glass sample to define a transmitted polarization-switched light beam. The method also includes measuring an amount of power in the polarization-switched light beam to form a polarization-switched reference signal. The method further includes detecting the transmitted polarization-switched light beam to form a polarization-switched detector signal. The method additionally dividing the polarization-switched detector signal by the polarization-switched reference signal to define a normalized polarization-switched detector signal. The method also includes processing the normalized polarization-switched detector signal to determine the profile characteristic of the glass sample.

Another aspect of the disclosure is a method of measuring a profile characteristic of a glass sample disposed adjacent a reference block. The method includes generating a polarization-switched light beam that is switched between orthogonal polarizations at a rate of between 1 Hz and 50 Hz. The method also includes measuring an amount of power in the polarization-switched light beam and generating a polarization-switched reference signal, wherein the measured amounts of power in each of the orthogonal polarizations are within 50% of each other. The method further includes transmitting the polarization-switched light beam through the glass sample and reference block for different depths into the glass sample. The method additionally includes relaying the transmitted polarization-switched light beam to a signal photodetector using a relay optical system, with the signal photodetector generating a polarization-switched detector signal. The method also includes dividing the detector signal by the reference signal to form a normalized detector signal. The method also includes determining the profile characteristic of the glass sample from the normalized detector signal.

Additional features and advantages will be set forth in the Detailed Description that follows and in part will be readily apparent to those skilled in the art from the description or recognized by practicing the embodiments as described in the written description, the claims thereof and the appended drawings.

It is to be understood that both the foregoing general description and the following Detailed Description are merely exemplary and are intended to provide an overview or framework for understanding the nature and character of the claims.

BRIEF DESCRIPTION OF THE DRAWINGS

The accompanying drawings are included to provide a further understanding and are incorporated in and constitute a part of this specification. The drawings illustrate one or more embodiment(s), and together with the Detailed Description serve to explain the principles and operation of the various embodiments. As such, the disclosure will become more fully understood from the following Detailed Description, taken in conjunction with the accompanying Figures, in which:

FIG. 2A is a close-up, front-on view of an example confocal aperture;

FIGS. 2B and 2C are close-up, front-on views of examples of the first and second aperture stops, respectively;

FIG. 5A is a plot of power P (μm) versus incident angle $\theta$ (degrees) for TE polarization (indicated by +) and TM polarization (indicated by ○) for a high-quality power meter when illuminated with a narrow beam of collimated light that under-fills the photodetector;

FIG. 5B is a plot of the difference in measured power $\Delta P$ (%) versus angle for the TE and TM polarizations based on FIG. 5A;

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute a part of this

DETAILED DESCRIPTION

The entire disclosure of any publication or patent document mentioned herein is incorporated by reference.

Cartesian coordinates are shown in some of the Figures for the sake of reference and are not intended to be limiting as to direction or orientation.

Figure 1:
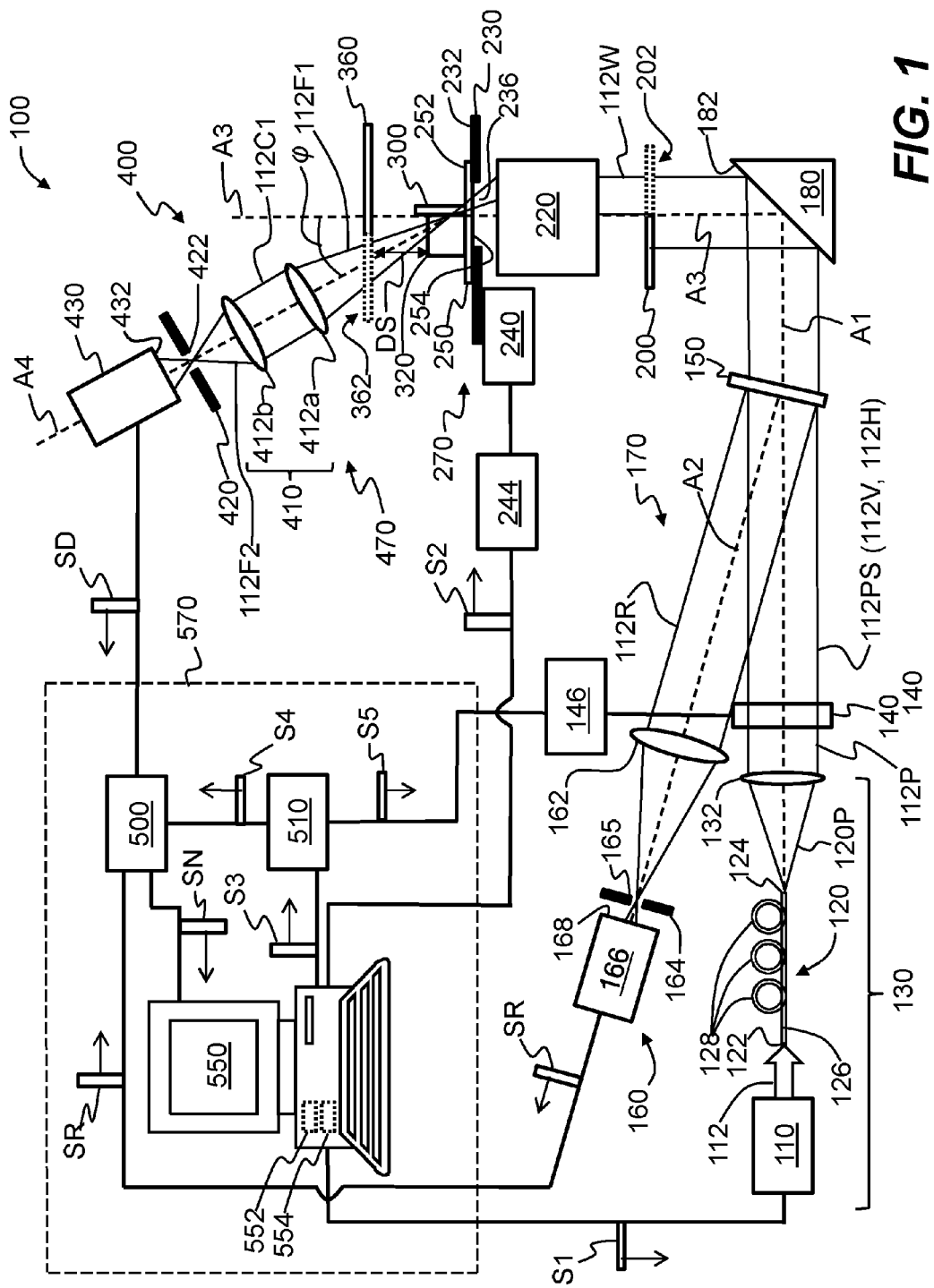
FIG. 1 is a schematic diagram of an example RNF measurement system according to the disclosure.

FIG. 1 is a schematic diagram of an example RNF measurement system ("system") 100 according to the disclosure. The system 100 is configured to determine a characteristic of a glass sample. The characteristic can be the refractive index profile for orthogonal polarizations of light, the birefringence or the stress. All three of these profile characteristics are related.

The system 100 includes a light-source system 130. The light-source system 130 includes a light source 110 that emits light 112 along a first optical axis A1. An example light source 110 is a single-mode, fiber pig-tailed laser operating at a nominal wavelength of 637 nm. The light-source system 130 also includes a polarization controller 120 having an input end 122 and an output end 124. The light source 110 is optically coupled to input end 122 of polarization controller 120. The polarization controller 120 receives light 112 from light source 110 and outputs polarized light 120P. An example polarization controller 120 is fiber based and includes a section of single-mode optical fiber 126 that is wrapped around fiber paddles 128 that induce stress birefringence into the optical fiber in order to create the desired output polarization.

The light-source system 130 also includes a collimating lens 132. The polarization controller 120 is optically coupled at its output end 124 to collimating lens 132. The collimating lens 132 is configured to receive divergent polarized light 120P emitted by single-mode optical fiber 126 of polarization controller 120 and forms a collimated, free-space polarized light beam 112P, which in an example has a generally circular cross-sectional shape. The collimating lens 132 can include one or more lens elements or other types of optical elements, such as reflective elements.

The system 100 also includes a polarization switch 140, which is located downstream of collimating lens 132 along axis A1 so that it receives collimated polarized light beam 112P. The polarization switch 140 is operably connected to and driven by a polarization-switch controller 146 that in an example operates a switching rate of as high as 1 KHz, but in another example operates between 1 Hz and 50 Hz. The polarization switch 140 and polarization-switch controller 146 constitute a polarization switching system. In an example, polarization switch 140 is in the form of a variable retarder, such as a liquid-crystal variable retarder. Other types of known polarization switches can be employed, such as fiber-optic-based switches, electro-optic switches and mechanically rotatable polarizers.

The polarization switch 140 is driven by polarization-switch controller 146 to switch the polarization state of polarized light beam 112P back and forth between TE and TM polarizations (i.e., vertical and horizontal polarizations) 112V and 112H. The polarized light beam 112P is thus converted to a polarization-switched light beam 112PS. An example switching time of the polarization switch 140 is between 1 millisecond and 100 milliseconds, with an exemplary switching time being about 1 millisecond. In an example, polarized light beam 112P leaves polarization controller 120 as either TE or TM polarized light, and polarization switch 140 switches the polarized light beam 112P to the other polarization when activated, i.e., to polarization-switched light beam 112PS.

The system 100 further includes along axis A1 and downstream of polarization switch 140 a beam-splitting element 150. An example beam-splitting element 150 is very thin, e.g., an uncoated pellicle. The beam-splitting element 150 is configured to reflect a relatively small portion ("reflected light portion") 112R of polarization-switched light beam 112PS along a second optical axis A2. In an example, reflected light portion 112R is up to 50% of polarization-switched light beam 112PS, but in other examples reflects less than 20% or less than 10% of the polarization-switched light beam, with 8% being an exemplary amount.

In an example, second optical axis A2 makes a relatively shallow angle with first optical axis A1, i.e., the polarization-switched light beam 112PS is near-normally incident upon the beam-splitting element 150. This helps to ensure that the reflection of the TE and TM polarization states from beam-splitting element 150 is about the same. This is because the difference in reflectance of TM and TE light changes strongly with increasing angle. A thin beam-splitting element 150 has the benefit that ghost reflection offsets from multiple reflections between its two surfaces are negligible.

Arranged along second optical axis A2 is a reference detector system 160 that in an example includes, in order along the second optical axis, a focusing lens 162 having a focal length f1, a confocal aperture 164 arranged a distance f1 away from the focusing lens, and a reference photodetector 166 that has a photosensitive surface 168. The reference detector system 160 is configured to receive and detect polarization-switched reflected light portion 112R that is reflected by beam-splitting element 150 to travel along optical axis A2. In an example, focusing lens 162 is achromatic.

Figure 2D:
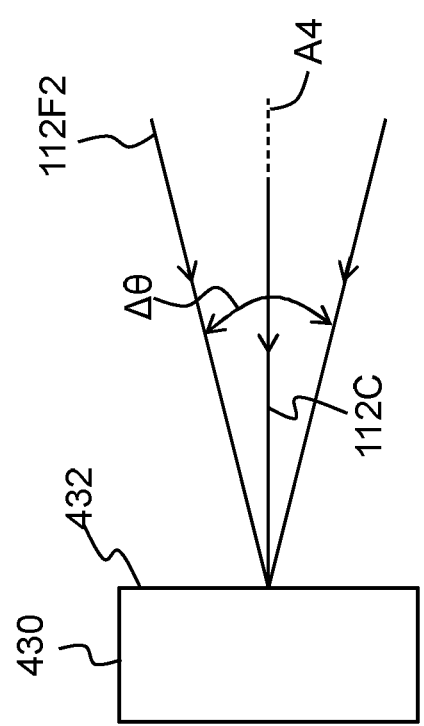
FIG. 2D is a close-up side view of the signal photodetector showing the focused polarization-switched light beam incident on the signal photodetector with its central ray at normal incidence, and showing the range of angles $\Delta\theta$ in the focused polarization-switched light beams.

FIG. 2A is a close-up, front-on view of an example confocal aperture 164. The confocal aperture 164 has a small on-axis opening 165. The second optical axis A2 and reference detector system 160 define a reference arm 170 of system 100. The reference photodetector 166 generates a polarization-switched reference signal SR in response to receiving reflected polarization-switched light portion 112R.

The system 100 also includes a light-turning member 180 arranged downstream of beam-splitting element 150 along first optical axis A1. The light-turning member 180 defines a third optical axis A3 that in an example makes a right angle with first optical axis A1. An example light-turning member 180 is a mirror having a reflecting surface 182. The light-turning member 180 serves to reflect polarization-switched light beam 112PS such that the light beam travels along third optical axis A3.

The system 100 also includes a first sectorial aperture stop 200 disposed downstream of light-turning member 180 and along third optical axis A3. FIG. 2B is a close-up, front-on view of an example first aperture stop 200. The first aperture stop 200 has an off-axis first opening 202 that is wedge-shaped (see FIG. 2B). First opening 202 is configured to form from polarization-switch light beam 112PS a wedged-shaped polarization-switched light beam 112W. First opening 202 is configured to pass only the portion of polarization-switched light beam 112PS that has the potential to follow a trajectory to a signal detector 430 via a first-pass refraction through the measurement region and out of the top surface of a reference block 320 (signal detector and reference block 320 are introduced and discussed below).

Any light 112PS that would otherwise not refract out of a top 322 of reference block 320 on the first pass must be blocked by the opaque regions defining the wedge-shaped opening 202. The example wedge-shaped opening 202 has an apex 204 an an associated an angle η that in an example is adjustable, e.g., between 0° and 90°, so that the cross-sectional shape of the transmitted wedge-shaped polarized light beam 112W can be adjusted. The apex 204 of wedge-shaped opening 202 is located along third optical axis A3.

The system 100 also includes, along third optical axis A3 and downstream of first sectorial aperture stop 200, an objective lens 220 and a movable support platform 230 that is supported by a positioning stage 240 that is movable in the X, Y and Z directions (i.e., three dimensions). The positioning stage 240 is operably connected to a stage controller 244. Thus, positioning stage 240 is operable to move the support platform in three dimensions.

An example objective lens 220 is a microscope objective that is centered to be co-axial with third optical axis A3 and the apex 204 of first sectorial aperture stop 200. The support platform 230 has an upper surface 232 that supports a coverslip 250 having top and bottom surfaces 252 and 254. The support platform 230 has an aperture 236 through which polarization-switched light beam 112PS passing through first sectorial aperture stop 200 can pass and then pass through coverslip 250. The objective lens 220 is corrected for the presence of coverslip 250.

Figures 3A, 3B:
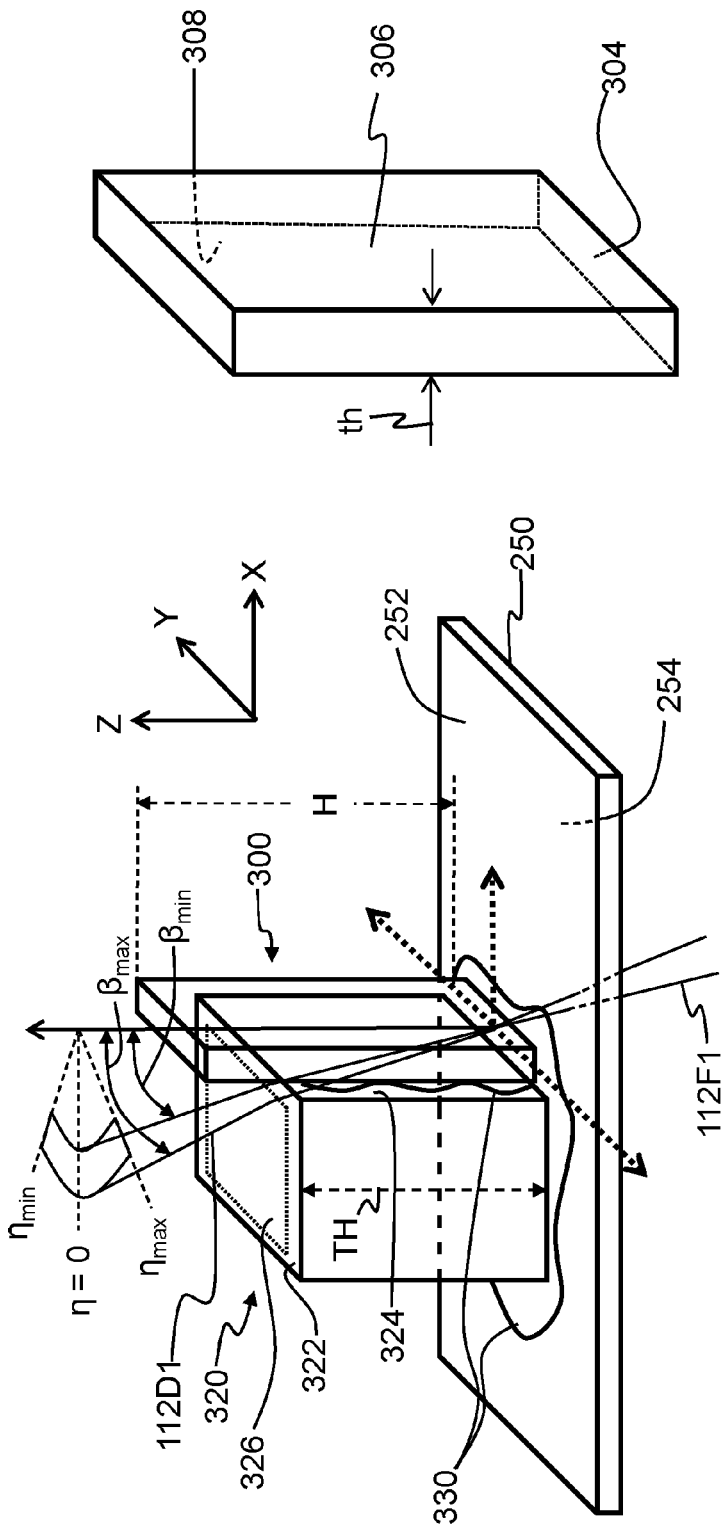
FIG. 3A is an elevated view of the reference block and glass sample as arranged atop the microscope slide in the RNF measurement system of FIG. 1.
FIG. 3B is an elevated view of the glass sample.

The system 100 also includes a glass sample 300. The glass sample 300 is supported on coverslip 250 along with reference block 320. FIG. 3A is a close-up, elevated view of glass sample 300 and reference block 320 disposed on top surface 252 of coverslip 250. FIG. 3B is a close-up, elevated view of just the glass sample 300. The glass sample 300 has an edge surface 304, a front surface 306 and a back surface 308. The glass edge surface 304 confronts the top surface 252 of coverslip 250.

The reference block 320 has the aforementioned top surface 322 and a front surface 324. The reference block 320 and glass sample 300 are arranged so that the front surface 324 of the reference block 320 confronts back surface 308 of the glass sample. The optical parameter to be measured has a gradient along the X-direction.

The glass edge surface 304 is measured in the X-Y plane. A scanning measurement of glass edge surface 304 can be made as a function of position. The glass sample 300 has a thickness th in the X-direction that is generally less than several millimeters. In an example, glass edge surface 304 is processed, e.g., cleaved and/or polished, to expose the depth of the stress profile extending along the edge 304 from the back surface 308 to the front surface 306.

Single or multiple raster scans can be made at a variety of positions over distances of several millimeters. Polar angle β and azimuthal angle η are shown in FIG. 3A, with example limits $\beta_{min}$, $\beta_{max}$ and $\eta_{min}$, $\eta_{max}$. The reference block 320 has a thickness TH in the Z-direction. An example range for the thickness TH is between 5 mm and 20 mm, with 8 mm being an exemplary thickness within the range.

In an example embodiment, an index-matching oil 330 is used to ensure low-reflection optical coupling between the coverslip 250, the edge surface 304 of the glass sample 300, the back surface 308 of the glass sample and the front surface 324 of the reference block 320. The coverslip bottom surface 254 and reference block top surface 322 may each be optionally coated with a polarization-independent and angularly independent anti-reflection (AR) coating 326 (shown with a dotted-line boundary) to minimize the reflectance variations for polarization and ranges of incident angles.

The polarization-switched light beam 112PS passes off-axis through wedge-shaped opening 202 of first sectorial aperture stop 200 and the resultant wedge-shaped polarization-switched light beam enters objective lens 220, which is centered on third optical axis A3. The width of polarization-switched light beam 112PS is such that it overfills the input clear aperture (not shown) of objective lens 220. This overfilling ensures that only the most intense and roughly uniform, substantially Gaussian center-portion of polarization-switched light beam 112PS is focused onto edge surface 304 of glass sample 300 as a focused beam.

This overfilling also helps to reduce or eliminate any adverse diffractive effects from the outer circular portion of wedge-shaped opening 202. Because polarization-switched light beam 112PS enters objective lens 220 from an off-axis position relative to third optical axis A3, the objective lens forms a polarization-switched, first focused light beam 112F1.

The system 100 also includes a fourth optical axis A4 that intersects the third optical axis A3 at a focus position of objective 220, with the focus position being located on the edge surface 304 of the glass sample 300. A signal detector system 400 is operably arranged along fourth optical axis A4. An example signal detector system 400 includes, in order along fourth optical axis A4, a relay optical system 410, a confocal variable aperture 420 with an on-axis opening 422, and a signal photodetector 430 that has a photosensitive surface 432. In an example, relay optical system 410 is achromatic. An example achromatic relay optical system 410 as shown in FIG. 1 includes a pair of lens elements 412a and 412b. In an example, each lens element 412a and 412b has a focal length f2 (e.g., f2=80 mm) and includes antireflection coatings. An example diameter (clear aperture) of lens elements 412a and 412b is about 2 inches.

In the example two-lens embodiment of relay optical system 410, the first lens 412a is located a focal-length f2 away from where the axes A4, A3, focus position 260 and the glass edge surface 304 intersect. The first lens 412a receives and collimates polarization-switched focused light beam 112F1 to form a collimated light beam 112C1 without vignetting. The second lens element 412b is arranged so that it receives collimated light beam 112C1 and re-focuses the beam to form a second polarization-switched focused light beam 112F2. The second polarization-switched focused light beam 112F2 passes through confocal variable aperture 420 and is received and detected by signal photodetector 430. In response, signal photodetector 430 generates a polarization-switched detector signal SD. In an example, signal photodetector 430 is placed slightly beyond the focusing point of the second lens element 412b.

The system 100 also includes a second sectorial aperture stop 360 downstream of reference block 320 and glass sample 300 and along third optical axis A3. FIG. 2C is a close-up, front-on view of an example second sectorial aperture stop 360. The second sectorial aperture stop 360 includes a second opening 362 that is offset from the center of the stop and whose azimuthal pass angle range may be fixed or manually adjustable. An example second sectorial aperture stop 360 has an arcuate shape. The fourth axis A4 passes nominally through the center of the second arcuate-shaped opening 362.

In an example, second sectorial aperture stop 360 includes two semicircular movable portions 364 and a central disk 366. A central fastening member 368 secures the semicircular portions 364 so that they can rotate to open and close second opening 362 (as indicated by the bold arrows) while keeping opening edges 369 directed radially to the third optical axis A3 of the beam at all angular positions.

The first sectorial aperture stop 200, objective lens 220, moveable support platform 230, coverslip 250, positioning stage 240, and second sectorial aperture stop 360 constitute a scanning optical system 270.

In an example, second opening 362 has the aforementioned arcuate shape with an associated nominal azimuthal passband angle of 36° (+/−18°) and a minimum polar pass angle $\beta_{min}$ of 26°. In an example, second opening 362 has a smaller area than first opening 202 of first sectorial aperture stop 200. This configuration serves to block diffracted light that arises from the interaction of polarization-switched light beam 112PS passing the edges of wedge-shaped opening 202 of first sectorial aperture stop 200. Such diffracted light can adversely impact the measurement. The polarization-switched focused light beam 112F1 that leaves objective lens 220 and travels along fourth optical axis A4 passes through aperture 236 of movable support platform 230, through coverslip 250 and reaches glass edge surface 304 of glass sample 300. The refractive index profile(s) that is (are) to be measured lie(s) along the plane of glass edge surface 304.

After the focal point, the polarization-switched focused light beam 112F1 diverges and continues through front surface 324 of reference block 320 and exits top surface 322. A portion of polarization-switched focused light beam 112F1 then passes through second opening 362 of second sectorial aperture stop 360.

The portion of polarization-switched focused light beam 112F1 propagating at polar angles less than $\beta_{min}$ is blocked, while the portion propagating at angles greater than $\beta_{min}$ passes to signal photodetector 430. Thus, if the refractive index at glass edge surface 304 decreases, then the refraction angle of the rays from the polarization-switched focused light beam 112F1 increase and more optical power manages that is otherwise blocked now exceeds the minimum polar angle $\beta_{min}$. This causes the optical power at signal detector 430 to increase. Conversely, if the refractive index at glass edge surface 304 increases, then the refraction angle of the rays from the focused light beam 112F1 decreases and less optical power manages to exceed the minimum polar angle $\beta_{min}$ and is blocked by the second aperture stop 360. This causes the optical power at signal detector 430 to decrease.

The second sectorial aperture stop 360 is arranged at a distance DS from the top surface 322 of reference block 320. In an example, distance DS is in the range from 8.5 mm to 37.5 mm. However, the distance DS can be such that a sample having a height H of up to 3 inches can be accommodated between coverslip 250 and second sectorial aperture stop 360, where the limitation is defined by the instance of the aperture stop intersecting the first lens element 412a.

The confocal variable aperture 420, which can be an adjustable iris, is disposed at the focal point of the relay optical system 410 (e.g., a distance f2 behind second lens element 412b) to create a confocal signal detection arrangement. Note that reference detector system 160 also has a confocal detection arrangement, but with only one focusing lens 162 because the polarization-switched reflected beam portion 112R from beam-splitting element 150 is already collimated. The signal detector system 400 and fourth optical axis A4 define a signal arm 470 of system 100.

In an example, on-axis opening 165 of confocal aperture 164 can be stopped down to approximately 1 mm in diameter or even smaller. The confocal detection arrangement for signal detector system 400, combined with the large offset distance (e.g., about 200 mm) of signal photodetector 430 from the location of the sample measurement area serves to prevent the majority of any undesirable scattered and reflected light from the measurement area from reaching reference photodetector 166 and signal photodetector 430. This serves to eliminate measurement errors owing to scattered light and/or reflected light.

A problem common to all photodetectors is that the efficiency of the photodetection varies over the face of the photodetector. Generally, the larger the photodetector is, the more the detection uniformity can vary across the face. In high-quality photodetectors, variations in detection uniformity over 1 cm$^2$ can be approximately ±2%. These uniformity variations impart an error to the measured optical power versus refracted angle and therefore contribute to error in the scaling of the measured index of refraction.

In principle, these kinds of inherent detection errors can be reduced or eliminated through a calibration process. This calibration step can include scanning a glass sample of a known refractive index profile and then re-mapping the measured sample data to improve the accuracy. However, it would be most desirable to avoid this added step by keeping the illuminated area of the detector as small as possible.

Figures 4A, 4B:
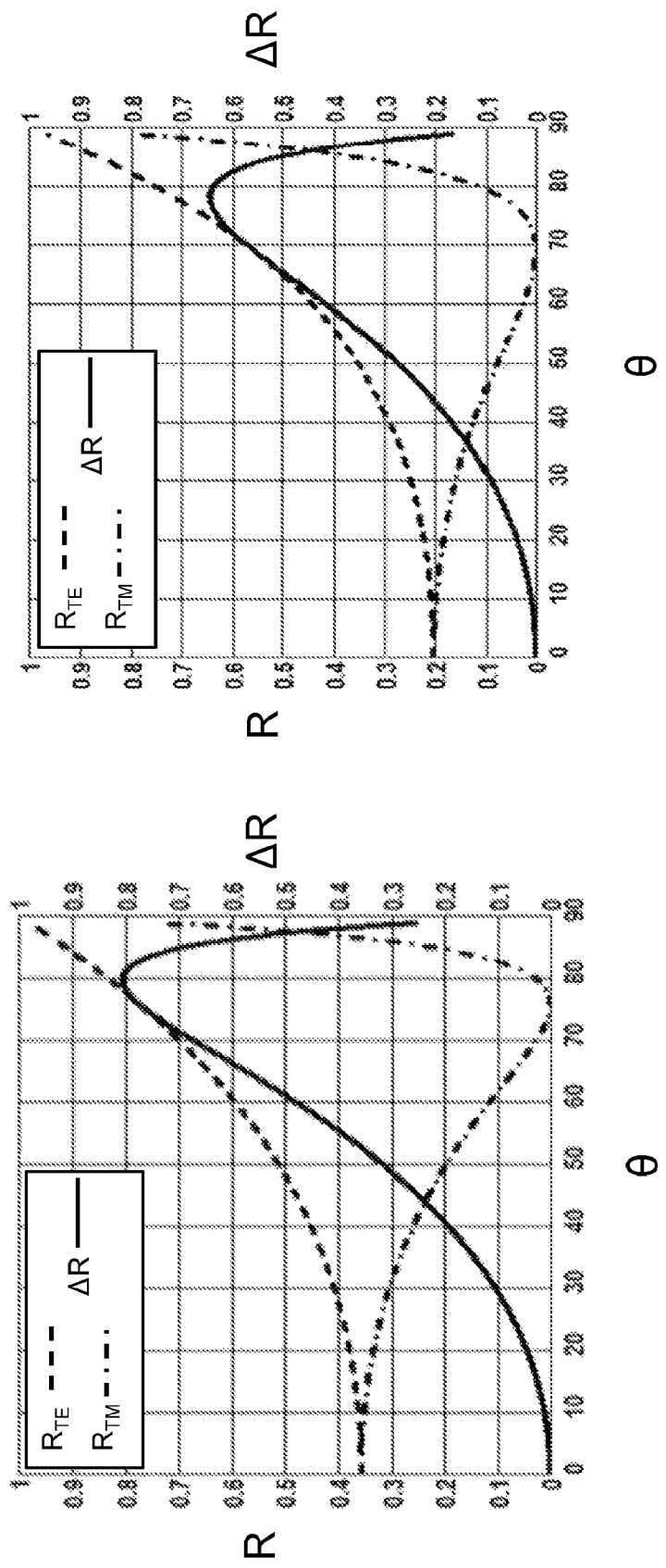
FIGS. 4A and 4B are plots of reflectivity R versus angle (degrees) for TE-polarized light, TM-polarized light and the reflectivity difference $\Delta R = (R_{TE} - R_{TM})$ for a silicon-air interface (FIG. 4A) and an interface between silicon and a medium having a refractive index of 1.5 (FIG. 4B)

FIG. 4A is a plot of reflectance R on the left-hand axis and $\Delta R = R_{TE} - R_{TM}$ on the right-hand axis as a function of incident angle θ (in degrees) for an interface between air and silicon that is present at a silicon-based photodetector. FIG. 4B is the same type of plot but for an interface between silicon and a medium having a refractive index of 1.5 (e.g., index-matching oil or glass). The TE reflectance $R_{TE}$ is represented as a dashed line, the TM reflectance $R_{TM}$ is represented as a dashed-dotted line and the difference in TE and TM reflectivity $\Delta R$ is represented as a solid line. As can be seen from FIGS. 4A and 4B, low angles of incidence have a low value of $\Delta R$ and so are preferred for light that is incident upon a silicon-based photodetector. To this end, and with reference to FIG. 2D, signal photodetector 430 is arranged along fourth optical axis A4 so that a central ray 112C of focused light beam 112F2 is incident nearly perpendicularly to the signal photodetector for all incident angles θ in the range Δθ of the focused light beam.

Furthermore, the polar angle range Δβ of incident angles β that are incident upon signal photodetector 430 is halved from the 12° usually associated with prior art systems to approximately 6°, because the incident angles are split between positive and negative angles about the surface normal. This reduces the maximum difference between measured TE and TM powers from over 3.1% to approximately 0.25%, which is an improvement of about a factor of 12. In the azimuthal range Δη, the incident angle η decreases from the ±45° usually associated with the prior art to ±18°.

FIG. 5A is a plot of power P (μm) versus incident angle θ (degrees) for TE polarization (indicated by +) and TM polarization (indicated by ◯) for a high-quality power meter illuminated with a narrow beam of collimated light that underfills signal photodetector 430. A computer-controlled liquid-crystal variable retarder was used to modulate the incident light between the TE and TM polarization states multiple times at each angle. Because the angle was rotated by hand, the incident angles θ are indicated on the graph above and below the power levels.

FIG. 5B is a plot of the difference in measured power ΔP (%) versus angle for the TE and TM polarizations based on FIG. 5A. The minimum-to-maximum difference in ΔP is about 3.1% over the +/−24° range. An artifact of back reflection off of the liquid crystal polarization rotation element occurred at zero degrees as indicated by an arrow AR1 in FIG.

5A. This artifact changed the power levels, but as expected for normally incident light it did not affect the power difference ΔP.

The calculated improvement in decreasing the TM and TE power biases can be estimated from the plots of FIGS. 4A, 4B, 5A and 5B. For instance, with respect to FIG. 4A, ΔR drops from 25.0% at 45° to 3.6% at 18° degrees, which is an improvement of a factor of 6.9.

The adjustable azimuthal bandpass Δη allows a user to decrease the azimuthal pass-band range of angles in order to diminish polarization differences in detection efficiency. In an example, focal length f1 of focusing lens 162 and focal length f2 of relay optical system 410 are relatively long (e.g., 75 mm to 80 mm) so that the incident angles of a focused arcuate light 112A at signal photodetector 430 are relatively small. This serves to minimize polarization and angle-dependent efficiency errors in the detection and reference arms.

Another advantage of the adjustable second aperture stop 360 is that the arcuate opening 362 can be closed down in the azimuthal direction Δη to ensure that the refracted light does not exceed the clear aperture of relay optical system 410.

In an example, relay optical system 410 has 1× magnification. However, other magnifications may be used to further decrease the incident angles at the signal photodetector 430 and thus further decrease angular and polarization measurement errors. The confocal arrangement of reference detector system 160 and signal detector system 400 helps to limit the amount of stray light that reaches the reference photodetector 166 and the signal photodetector 430. In an alternative embodiment, signal photodetector 430 and/or reference photodetector 166 are small-area detectors (e.g., 1 mm×1 mm) and the confocal apertures are not used.

Figures 6A, 6B:
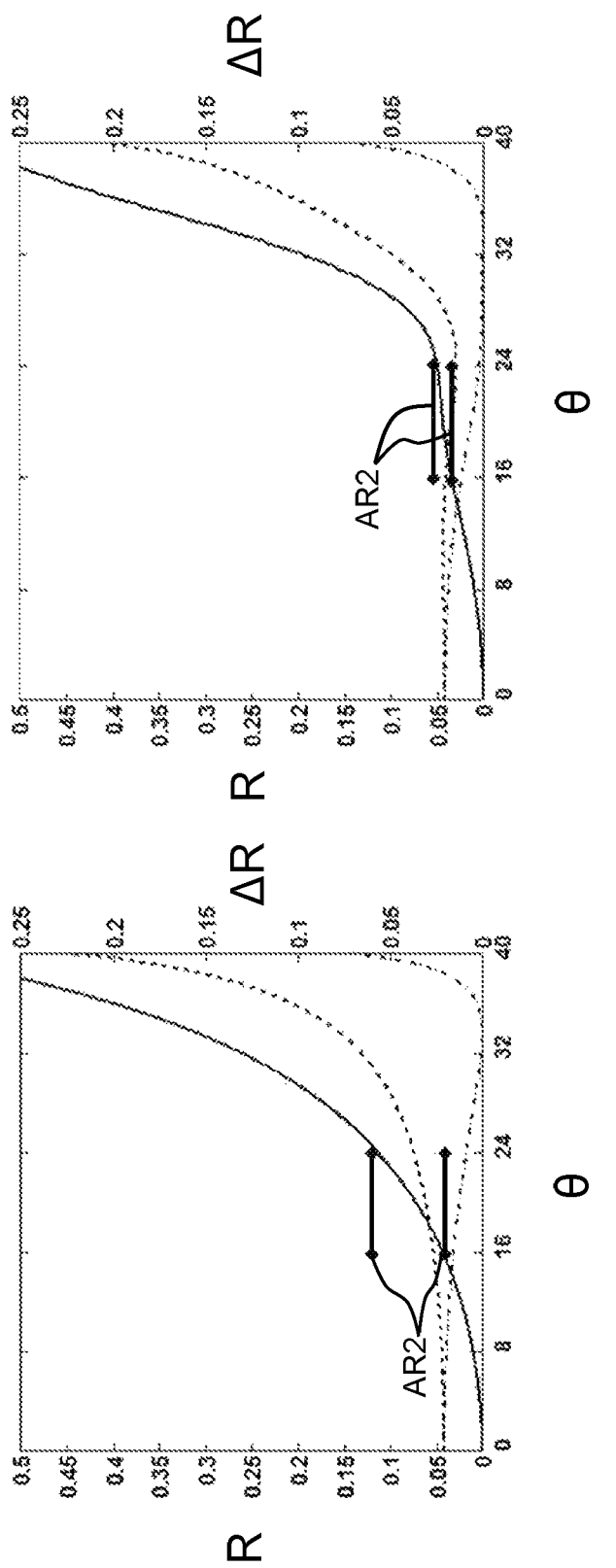
FIG. 6A plots reflectivity R versus incidence angle $\theta$ (degrees) for an interface between a reference block having a refractive index of 1.51 and air.
FIG. 6B is the same as FIG. 6A but with an anti-reflection (AR) coating at the interface, the AR coating being made of a single layer of $MgF_2$ having a thickness of 915 nm optimized for light having a wavelength $\lambda$ of 633 nm (i.e., the AR coating has a thickness of 1.45λ)

As mentioned above, an AR coating 326 may be applied to the top surface 322 of reference block 320. FIG. 6A plots reflectance R versus incident angle θ (degrees) for an interface between reference block 320 of refractive index 1.51 and air. FIG. 6B is the same plot as FIG. 6A but with an AR coating 326 made of a single layer of $MgF_2$ having a thickness of 915 nm optimized for light having a wavelength λ of 633 nm (i.e., 1.45λ). The TE reflectance is represented as a dashed line, while the TM reflectance is measured as a dashed-dotted line. The TE-TM reflectance difference ΔR is represented by a solid line, and the ΔR axis is on the right-hand side of the plots. Arrows AR2 show the range of incident angles Δθ between 16° and 24°, which is typical for the beam when refracting into the air from within the reference block 320.

A standard quarter-wave, AR coating 326 of $MgF_2$ on top surface 322 of reference block 320 can diminish the internal polarization reflection differences over the span of angles. However, the goal of a birefringence measurement is ultimately to diminish both the angular and the polarization reflection differences across the range of angles as much as possible. In FIG. 6A, reflectivity R varies by 3.5% over the angular range Δθ. However, by use of the 1.45λ thickness $MgF_2$ AR coating 326, the variation in ΔR over the angular range Δθ is reduced more than 4×, to 0.8%. By comparison, a standard quarter-wave AR coating 326 would achieve only a 2× reduction, to 1.6%, over the same angular range.

With reference again to FIG. 1, system 100 includes a dual-channel power meter 500 that is electrically connected to signal photodetector 430 and reference photodetector 166. The dual-channel power meter 500 is also electrically connected to a master-trigger controller 510, which is also electrically connected to polarization-switch controller 146. The system 100 also includes a main computer-controller 550 that is operably connected to positioning stage controller 244, dual-channel power meter 500 and master-trigger controller 510.

In an example, main computer-controller 550 includes a processor 552 and a memory unit ("memory") 554 configured to execute instructions stored in firmware and/or software, including signal-processing instructions for carrying out the measurements disclosed herein. In examples, the terms "controller" and "computer" are interchangeable.

The main computer-controller 550 is programmable to perform the functions described herein, including the operation of system 100 and the measuring of the surface stress, refractive index profile and/or birefringence. As used herein, the term "computer" is not limited to just those integrated circuits referred to in the art as computers but broadly refers to computers, processors, microcontrollers, microcomputers, programmable logic controllers, application-specific integrated circuits and other programmable circuits, and these terms are used interchangeably herein.

Software may implement or aid in the performance of the operations of system 100 as disclosed herein. The software may be operably installed in controller 550 and in particular in processor 552 and memory 554. Software functionalities may involve programming, including executable code, and such functionalities may be used to implement the methods disclosed herein. Such software code is executable by the general-purpose computer or by processor 552.

The main computer-controller 550, dual-channel power meter 500 and master-trigger controller 510 constitute an example of a signal control and processing system 570, as indicated by the dashed-line box. The main computer-controller 550 can also include polarization-switch controller 146 and stage controller 244.

In an example, light source 110 emits a continuous-wave (CW) light beam 112. However, in another example, light beam 112 may be pulsed and controlled during the measurement of the glass sample 300 using system 100. In one example, light source 110 is activated by main computer-controller 550 sending a light-source control signal S1 to the light source that causes the light source to emit light 112. Alternatively, light source 110 can be manually activated.

The controller 550 sends a stage control signal S2 to stage controller 244, which in response controls the movement of the positioning stage 240 during the measurement process. In an example, the movement of positioning stage 240 is used to scan the moveable support platform 230 through the focused wedge-shaped polarized light beam 112W, thus moving the focal point across the glass edge surface 304 of glass sample 300.

At each position, controller 550 then sends a control signal S3 to master-trigger controller 510, which synchronizes the operation of dual-channel power meter 500 and polarization-switch controller 146 via respective control signals S4 and S5 so that system 10 knows which polarization (TE or TM) is being measured at a given time. In an example, dual-channel power meter 500 uses a 1 kHz low-pass filter (not shown) to average over power variations in the kHz-and-higher frequency ranges. The low-pass filter is purposefully set equal to the fastest switching rate (1 kHz) of polarization-switch controller 146. This ensures maximum averaging over high-frequency signals while still enabling dual-channel power meter 500 to quickly respond to the polarization-state-specific signal and reference optical powers in the shortest time possible after the polarization state has been switched.

A 20-millisecond-to-100-millisecond delay is imposed between the time the polarization is switched and the time dual-channel power meter 500 is triggered to sample a reading. This delay ensures that the polarization has switched and that the response of dual-channel power meter 500 has settled to accurately read the optical power associated with the present polarization state of the measurement. Imposing this delay limits the maximum scan rate to approximately 10 to 50 measurements per second.

The power measured by signal photodetector 430 is embodied in electrical polarization-switched detector signal SD and the power measured in the reflected beam portion 112R by reference photodetector 166 is embodied in electrical polarization-switched reference signal SR. The electrical polarization-switched detector signal SD and electrical polarization-switched reference signal SR are sent to dual-channel power meter 500, which divides the electrical polarization-switched detector signal by the electrical polarization-switched reference signal for each polarization. This normalizes out any temporal power variations from light source 110, as well as any polarization-dependent transmittance differences through polarization switch 140. The resulting normalized polarization-switched signal SN is sent from dual-channel power meter 500 to main computer-controller 550 for processing.

Both the electrical polarization-switched reference signal SR and the electrical polarization-switched detector signal SD are read simultaneously by virtue of the master-trigger controller 510 triggering the dual-channel power meter 500 in a sample-and-hold-type method. This approach has the advantage of enabling sub-millisecond sampling of both the detector signal channel and the reference signal channel, which diminishes errors due to thermo-mechanical drift, vibrational errors in the scanning system, high-frequency laser power oscillations, low-frequency power drift and many other time-dependent errors that may impair index, birefringence and stress-measurement accuracy.

The normalized polarization-switched signal SN contains information about the refractive index profile for both the TE and TM polarizations by virtue of the reference and detector signals SR and SD being polarization-switched signals. The refractive index profile for each polarization is calculated by controller 550 based on the data embodied in normalized polarization-switched signal SN using techniques known in the art.

In an example, the measurement scan is extended outside of glass sample 300 to include two reference regions that have precisely known indices of refraction. It is desirable that these two regions consist of homogeneous, isotropic non-birefringent media. In an example, the two regions are a portion of the reference glass block 320 and a portion of index-matching oil 330. The indices of refraction of the two reference regions ($n_1$ and $n_2$) should be near to, but slightly different from, one another. Scaling factors M transform the measured power into the refractive index for each polarization state. The scaling factors M are determined by the two-point calibration process of taking the ratio of the difference in refractive indices of the two reference scan regions to the difference in the optical power ratios (signal power $P_{1,sig}$/reference power $P_{2,ref}$) as measured when [each polarization state is?] scanning through those reference regions:

$$M=(n_1-n_2)/(P_{1,sig}/P_{1,ref}-P_{2,sig}/P_{2,ref}).  \quad [EQ. 1]$$

Each polarization state has a slightly different transmitted optical power when scanning through these reference regions, and thus the normalization of the refractive index to the normalized power should be carried out separately for each polarization state, leading to a different scaling factor ($M_{TE}$ and $M_{TM}$) for each profile. The difference in the TE and TM refractive index profiles $n_{TE}$ and $n_{TM}$ defines the amount of birefringence (profile) $B=\Delta n$ in glass sample 300. The calculation of the stress (profile) $\sigma$ in the glass sample is related to the birefringence B through the stress-optic coefficient SOC via the relationship $\sigma=B/SOC$.

In its most general form, the stress $\sigma$ and birefringence B are 3×3 tensors and are related to each other through a $4^{th}$-ranked stress-optic tensor. For glass samples 300 that have stress symmetry, there can be many degeneracies and zeros in the coefficients of the stress-optic tensor if the polarization of the measurement light that is incident upon the sample is carefully controlled. In some cases, certain non-zero coefficients of the stress-optic tensor are negligible when compared to others and can ignored. Thus, the otherwise intractable problem of measuring the stress profile $\sigma$ through birefringence measurements is made tractable because of geometrical symmetries and simplifications that can be made in the stress-optic tensor as it relates to the sample and optical method of interrogation.

In particular, in cases of stress symmetry in glass sample 300 and with the wave propagation (k-vector) and polarizations properly oriented within principle planes of stress, many of the stress optic tensor components are either zero, very small and/or are degenerate. In that case, the stress optic tensor, when multiplied out with the electromagnetic field equations, will reduce to an expression that has a single stress coefficient number, namely the stress optic coefficient SOC, which relates the local birefringence to the stress in the glass through the above-identified relationship $\sigma=B/SOC$.

The stress-optic coefficient SOC is unique for each glass composition. However, the magnitude for most glasses generally ranges from $2.5\times10^{-6}$ to $3.5\times10^{-6}$ birefringence refractive index units (RIU) per mega-Pascal (MPa). Table 1 below shows the achievable stress-measurement accuracy or resolution that is associated with various orders of birefringence accuracy or resolution, given a nominal stress-optic coefficient SOC of $3.0\times10^6$ birefringence (RIU/MPa).

TABLE 1

| B (RIU)  | $\sigma$ (MPa) |
|----------|----------------|
| 0.001    | 333            |
| 0.0001   | 33.3           |
| 0.00001  | 3.33           |
| 0.000001 | 0.333          |

An advantage of system 100 is that it can use less precise positioning control of glass sample 300, because there is no need to acquire TE and TM scans in series to measure stress in the sample. The TE and TM measurements occur almost simultaneously (i.e., within about 10 to 50 milliseconds of each other) and at precisely the same location. Using the method of first measuring at one polarization state and then going back to measure at the other polarization state requires the use of a very precise and repeatable positioning method and apparatus, such as one that includes piezoelectric positioners.

Generally, piezoelectric positioners would limit the scan upper range to a maximum of 500 micrometers, which would not be useful for measuring many types of stress-strengthened glass products. Thermal drift and other time-dependent errors are also much larger if the two polarization scans are performed sequentially rather than simultaneously.

It has also been observed that integrating the measured optical power for a brief interval of 100 ms for each polarization state at a given position leads to more noise in the birefringence and stress profiles rather than less as one might expect. This is attributable to the fact that integrating the power for each polarization state also generates a greater separation in time between the measurements of the signal powers of the two polarization states, which diminishes the common-mode rejection advantages of the measurement systems and methods disclosed herein.

Figures 7A, 7B:
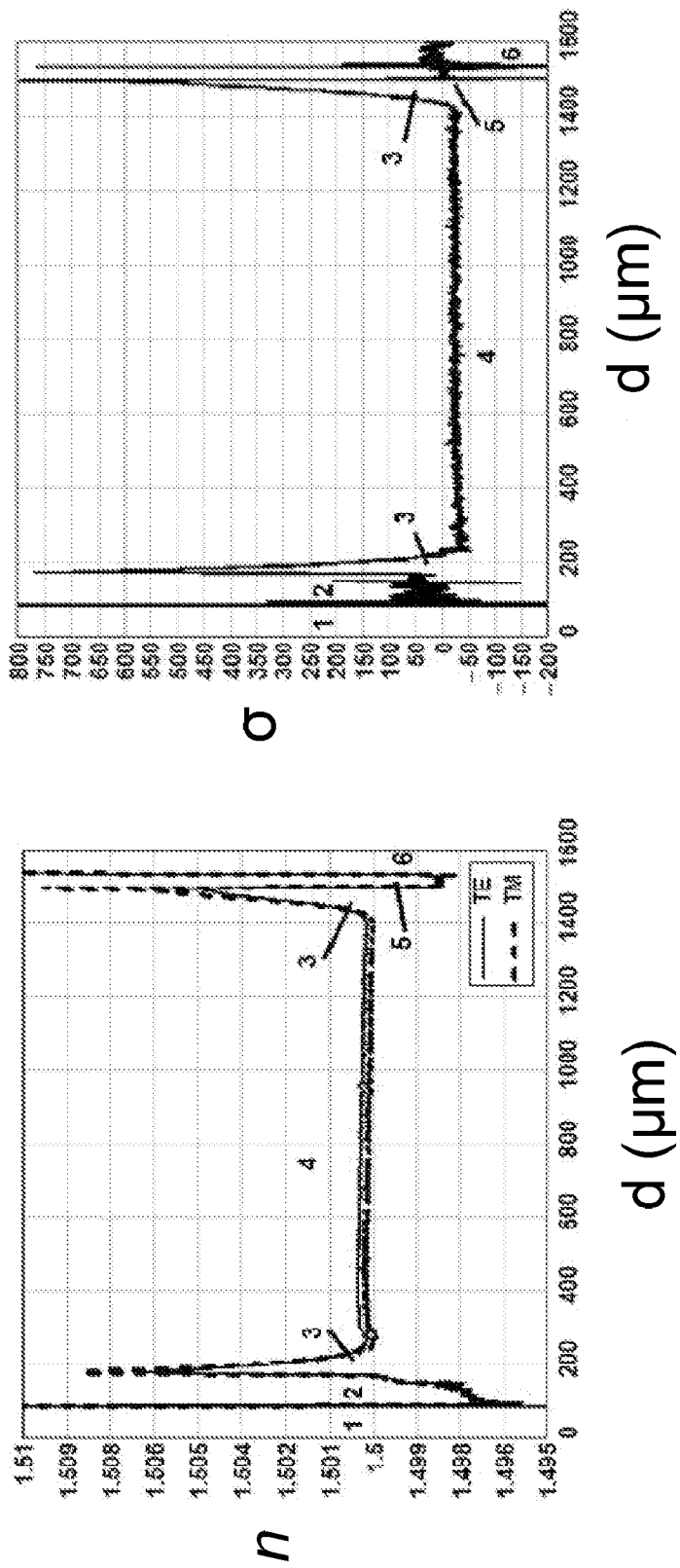
FIG. 7A is a plot of refractive index n (RIU) versus depth d (μm) into the glass sample, where the glass sample is a high-quality ion-exchanged glass (100% $KNO_3$), with the refractive index n for TE polarization (i.e., $n_{TE}$) indicated by a solid line and the refractive index n for TM polarization (i.e., $n_{TM}$) indicated by a dashed line.
FIG. 7B is similar to FIG. 7A but plots the resulting stress profile σ (MPa) versus depth (μm) as calculated from the birefringence data of FIG. 7A.

FIG. 7A is a plot of refractive index n (RIU) versus depth d (μm) into the glass sample 300, where the glass sample is a high-quality ion-exchanged glass (e.g., 100% $KNO_3$ salt bath). The scan was performed over a distance of 1,600 μm, and the glass sample 300 was 1,326 μm thick. The refractive index n for TE polarization (i.e., $n_{TE}$) is indicated by a solid line, while the refractive index n for TM polarization (i.e., $n_{TM}$) is indicated by a dashed line. Thus, FIG. 7A includes birefringence data and is in fact a plot of the birefringence profile B.

FIG. 7B is similar to FIG. 7A but plots the resulting stress profile (i.e., σ (MPa) vs. depth (μm)) as calculated from the birefringence profile of FIG. 7A.

The plots of FIGS. 7A and 7B include six regions, denoted 1 through 6. Region 1 is air and so is not of interest. Region 2 is an oil meniscus at the air-sample interface and is not of interest. Regions 3 are the high-index/high-compression, ion-exchange regions at either side of the glass sample 300. Region 4 is the base (bulk) glass region, which is under tension. Region 5 is the oil layer between the glass sample 300 and the reference block 320. Region 6 is the reference block 320.

Figures 8A, 8B:
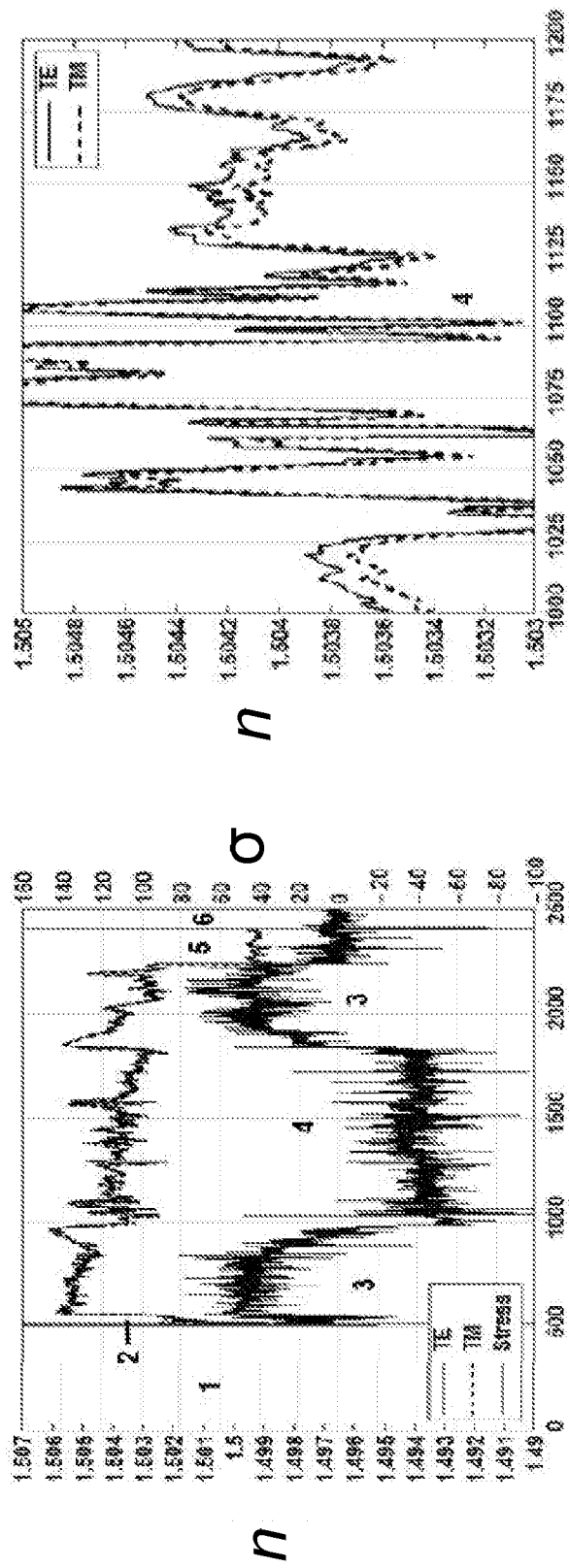
FIG. 8A is a plot of refractive index n (RIU) and stress σ (MPa) versus depth d (μm) into a glass sample consisting of two cladding glasses on either side of a core glass, with the refractive index profile at the top part of the plot and the stress profile at the bottom part of the plot.
FIG. 8B is the same as FIG. 8A and shows a magnification of the TE and TM refractive index profiles over a 200-μm span to reveal their common-mode variability and measured TM-TE birefringence.

FIG. 8A is a plot of refractive index n (RIU) and stress σ (MPa) versus depth d (μm) into a glass sample 300 that consists of two cladding glasses on either side of a core glass and spans 2,500 micrometers. FIG. 8B is the same as FIG. 8A but shows a magnification of the refractive index profiles over a 200-μm span to better reveal the measured birefringence and to illustrate the common-mode variability.

Even though the layered glass sample 300 has a lot of seeds (bubbles), a stress measurement can still be made. In FIG. 8A, the TE and the TM index profiles overlay each other and are barely discernible; they are better seen in the close-up view of FIG. 8B. The computed stress profile σ is on the bottom part of the plot. The following regions 1 through 6 are identified: region 1 is air; region 2 is the oil meniscus at the air-sample interface; regions 3 are the higher-index clad glasses on either side of the lower-index core, which is identified by region 4; region 5 is the oil layer between the glass sample 300 and the reference block 320; region 6 is the reference block 320.

The data in FIGS. 8A and 8B are tilted toward a lower index as the scan location increases (i.e., as depth d decreases). This occurs because the amount of optical power that reaches signal photodetector 430 increases with decreasing depth d due to the decreasing optical path length through the glass sample 300 as the scan progresses into the sample. Since the RNF measurement associates high optical power with low refractive index, the loss of optical power due to path-length dependent scattering shows up as a negative slope on the index of refraction profile.

However, the slope effect is eliminated in the birefringence profile because it is the difference between the index profiles of the two orthogonal polarizations. This allows not only for accurate measurements of the birefringence profile and stress profile in glass samples 300 that have optical inhomogeneity but also for determining the transmission loss profile through the glass sample from this data set, as well.

The close-up view of the refractive index data shown in the plot of FIG. 8B illustrates why the birefringence resolution is better than the index resolution. Acquiring index-of-refraction data at both polarizations nearly simultaneously and at the same location in the sample allows for significant common-mode signal rejection, which, in the present example, was due to inhomogeneities in the glass sample 300 itself.

Figure 9:
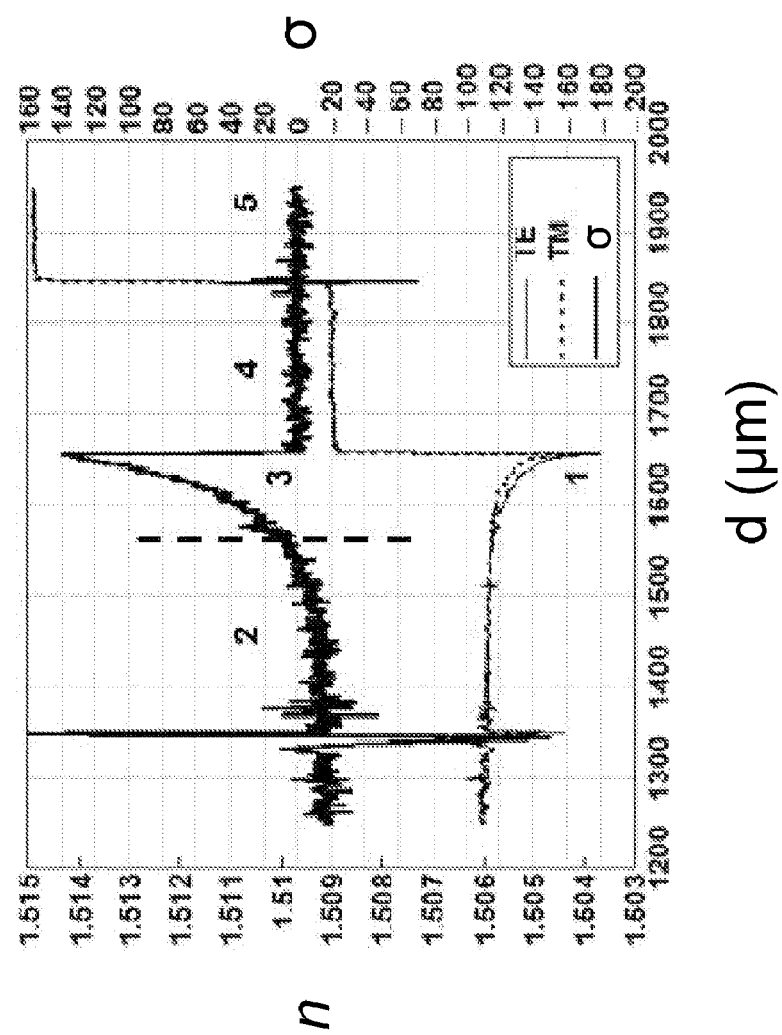
FIG. 9 is a plot similar to FIG. 8A and shows the refractive index profile (bottom part of the plot) and stress profile (top part of the plot) for a measured glass sample having a low-index layer at the surface.

FIG. 9 is a plot similar to that of FIG. 8A and shows the refractive index profile (bottom part of the plot) and stress profile (top part of the plot) for a measured glass sample 300 having a low-index layer at the surface. This type of glass sample 300 cannot be measured using prism-coupling techniques because the low-index surface layer cannot support any waveguide modes within the glass sample's surface region.

The glass sample 300 that was measured was a high concentration lithium-containing glass that was subject to an ion-exchange process. The TE and TM index profiles generally overlay one another for most of the scan, but are discernible near the surface at the location 1,650 μm. The following regions 1 through 6 are identified: region 1 is a low-index surface layer; region 2 is a region having tension; region 3 is an ion-exchange region of compression; region 4 is the index-matching oil with 152-μm coverslips used as spacers to create a mini-cell for the index-matching fluid; region 5 is the reference block 320.

The long-scanning capability of system 100, combined with the low-polarization sensitivity of the measurement, makes it possible to measure index, birefringence and stress profiles in two dimensions over a distance of millimeters into the sample.

Another advantage of system 100 is that, since both sides of glass sample 300 can be measured, it is possible to measure parts wherein the two sides have undergone different surface treatments using just one scan. Each side may be contrasted against the other without having to flip the glass sample 300 around to take a second measurement.

In addition, if one side of the glass sample 300 is opaque, is scattering or has an exceptionally high refractive index on the surface, it is still possible to obtain index, birefringence and stress data. One can place the less-than-perfect surface away from the reference block 320 (so that it is in contact with the air) and scan completely through the glass sample 300. While the opaque, scattering or high-index layer may not be measurable, the underlying substrate is measurable. Because the stress is transferred throughout the part by force balance, one may infer the stress imparted by the non-measurable region of the glass sample 300 by analyzing the rest of the sample, which is measurable.

The high-resolution index, birefringence and stress-measurement capability of system 100 enables new types of measurements to be made on a wide variety of glasses of various compositions and from various manufacturing processes. Glasses of essentially any index profile can be measured for stress, provided they are sufficiently transparent. Other prior art measurement techniques either fail to measure or have difficulty measuring glasses with low-index layers at the surface. In contrast, the system and methods disclosed herein are tolerant to some inhomogeneity in the glass sample due to seeds and other defects. Very thick samples can also be measured.

The 1-sigma, standard-deviation, index-of-refraction resolution was measured in an example system 100 as $\Delta n = 5 \times 10^{-5}$ RIU over scan distance of 100 micrometers. The 1-sigma standard-deviation of the birefringence resolution has been measured for an example system 100 as $\Delta n = 1.4 \times 10^{-5}$ RIU over scan distances of 100 micrometers in standard reference materials, which is 3.6 times better than the refractive index resolution and equates to approximately 4.6 MPa of stress resolution for standard, ion-exchanged glasses.

The birefringence resolution is better than the index resolution because acquiring index-of-refraction data at both polarizations nearly simultaneously and at the same location in the glass sample 300 allows for significant, common-mode signal rejection. Scans as long as 2.5 millimeters have been made through the entire thickness of stress-strengthened glass samples 300 of numerous types, with 1.0 to 1.5 micrometers of spatial resolution.

Longer-distance scans can be achieved simply by upwardly scaling the size of the components of system 100 and the glass samples 300.

It will be apparent to those skilled in the art that various modifications to the preferred embodiments of the disclosure as described herein can be made without departing from the spirit or scope of the disclosure as defined in the appended claims. Thus, the disclosure covers the modifications and variations, provided they come within the scope of the appended claims and the equivalents thereto.

What is claimed is:

1. A system for performing a refracted near-field (RNF) measurement of a profile characteristic of a glass sample disposed adjacent a reference block having a top surface, comprising:
    a light-source system that generates polarized light;
    a polarization-switching system that receives and switches the polarization of the polarized light between first and second orthogonal polarizations to form a polarization-switched light beam;
    a reference detector system arranged to receive a portion of the polarization-switched light beam and form a polarization-switched reference detector signal;
    an optical system configured to scan the polarized-switched light beam through the glass sample and the reference block at different depths into the glass sample;
    a signal detector system arranged to receive, over an angular range within 26° to 45° relative to normal incidence, the polarization-switched light beam transmitted through the glass sample and the reference block, and form in response a polarization-switched detector signal; and
    a signal-control-and-processing system operably configured to move the reference block and sample and receive and process the polarization-switched reference and detector signals to determine a profile characteristic of the glass sample.

2. The system of claim 1, wherein:
    the reference detector system includes a first confocal aperture operably disposed immediately adjacent a reference photodetector; and
    the signal detector system includes a first confocal aperture operably disposed immediately adjacent a signal photodetector.

3. The system of claim 1, wherein the signal detector system has a signal photodetector that is located at an axial distance between 80 mm and 200 mm from the top surface of the reference block.

4. The system of claim 1, wherein the signal-control-and-processing system includes:
    a computer-controller;
    a dual-channel power meter operably connected to the computer-controller, the signal detector system and the reference detector system; and
    a master trigger controller operably connected to the computer-controller, the dual-channel power meter and the polarization switching system.

5. The system of claim 1, wherein the optical system includes:
    a first aperture stop having a first off-axis aperture;
    an objective lens;
    a support platform that supports the reference block and glass sample;
    a positioning stage operably connected to the support platform and that is operable to move the support platform in three dimensions; and
    a second aperture stop having a second off-axis aperture having a size that is adjustable.

6. The system of claim 5, wherein the first off-axis aperture has a wedge shape and the second off-axis aperture has an arcuate shape.

7. The system of claim 1, wherein the detector optical system includes a signal photodetector, a confocal aperture, and a relay optical system, wherein the relay optical system receives and collimates the polarization-switched light beam transmitted through the glass sample and reference block and forms a focused polarization-switched light beam that passes through the confocal aperture and is incident upon a photosensing surface of the signal photodetector.

8. The system of claim 1, wherein the polarization-switching system includes a liquid-crystal variable retarder operably connected to a polarization-switch controller.

9. The system of claim 1, wherein the polarization-switching system switches the polarization of the polarization-switched light beam at a maximum rate of between 10 Hz and 50 Hz.

10. A method of measuring a profile characteristic of a glass sample disposed adjacent a reference block having a top surface, comprising:
    scanning a polarization-switched light beam through the glass sample and the reference block for different depths into the glass sample to define a transmitted polarization-switched light beam;
    measuring an amount of power in the polarization-switched light beam to form a polarization-switched reference signal;
    detecting the transmitted polarization-switched light beam to form a polarization-switched detector signal;
    dividing the polarization-switched detector signal by the polarization-switched reference signal to define a normalized polarization-switched detector signal; and
    processing the normalized polarization-switched detector signal to determine the profile characteristic of the glass sample.

11. The method of claim 10, wherein the reference block has a top surface, and wherein detecting the transmitted polarization-switched light beam includes receiving the transmitted polarization-switched light beam at a signal photodetector, wherein the signal photodetector resides at an axial distance of between 80 mm and 200 mm from the top of the reference block.

12. The method of claim 11, including focusing the transmitted polarization-switched light beam onto the signal photodetector.

13. The method of claim 11, including passing the transmitted polarization-switched light beam through a confocal aperture arranged immediately adjacent the signal photodetector.

14. The method of claim 10, wherein measuring an amount of power in the polarization-switched light beam included deflecting and detecting a portion of the polarization-switched light beam.

15. The method of claim 10, including further directing the transmitted polarization-switched light beam to be incident upon a signal photodetector at an incident angle of no greater than ±22.5°.

16. The method of claim 10, including passing the transmitted polarization-switched light beam through an anti-reflection coating on the top of the reference block, the anti-reflecting coating being configured to minimize differences in reflectivity between orthogonal polarizations of the transmitted polarization-switched light beam.

17. A method of measuring a profile characteristic of a glass sample disposed adjacent a reference block, comprising:
- generating a polarization-switched light beam that is switched between orthogonal polarizations at a rate of between 1 Hz and 50 Hz;
- measuring an amount of power in the polarization-switched light beam and generating a polarization-switched reference signal, wherein the measured amounts of power in each of the orthogonal polarizations are within 50% of each other;
- transmitting the polarization-switched light beam through the glass sample and reference block for different depths into the glass sample;
- relaying the transmitted polarization-switched light beam to a signal photodetector using a relay optical system, with the signal photodetector generating a polarization-switched detector signal;
- dividing the detector signal by the reference signal to form a normalized detector signal; and
- determining the profile characteristic of the glass sample from the normalized detector signal.

18. The method of claim 17, further comprising:
- passing the polarization-switched light beam through a first off-axis opening of a first aperture stop prior to passing the polarization-switched light beam through the glass sample;
- passing the transmitted polarization-switched light beam through a second off-axis opening of a second aperture stop prior to said relaying of the transmitted polarization-switched light beam.

19. The method of claim 18, wherein the first opening has a wedge shape and the second opening has an arcuate shape and an adjustable azimuthal angular extent.

20. The method of claim 17, wherein the transmitted polarization-switched light beam includes an angular range of within 22.5° about a central ray, and wherein the transmitted polarization-switched light beam is made incident upon the signal photodetector such that the central ray is substantially normally incident upon the signal photodetector.

* * * * *